United States Patent
Komatsu et al.

[11] Patent Number: 5,907,396
[45] Date of Patent: May 25, 1999

[54] OPTICAL DETECTION SYSTEM FOR DETECTING DEFECTS AND/OR PARTICLES ON A SUBSTRATE

[75] Inventors: Koichiro Komatsu, Tokyo; Hideyuki Tashiro, Yokohama; Tsuneyuki Hagiwara, Tokyo, all of Japan

[73] Assignee: Nikon Corporation, Tokyo, Japan

[21] Appl. No.: 08/934,454

[22] Filed: Sep. 19, 1997

[30] Foreign Application Priority Data

Sep. 20, 1996 [JP] Japan .................................. 08/271428

[51] Int. Cl.⁶ .................................................... G01N 21/00
[52] U.S. Cl. ................................... 356/237.1; 356/239.1; 356/239.7; 356/239.8
[58] Field of Search ..................................... 356/364–370, 356/237.1, 239.1, 239.3, 239.7, 239.8; 250/225, 560, 561

[56] References Cited

U.S. PATENT DOCUMENTS

| | | | |
|---|---|---|---|
| 3,814,946 | 6/1974 | Takahashi et al. | 250/572 |
| 3,879,131 | 4/1975 | Cuthbert et al. | 356/106 R |
| 4,468,120 | 8/1984 | Tanimoto et al. | 356/237 |
| 4,672,196 | 6/1987 | Canino | 250/225 |

FOREIGN PATENT DOCUMENTS 5-87549  5/1993  Japan .

*Primary Examiner*—Frank G. Font
*Assistant Examiner*—Michael P. Stafira
*Attorney, Agent, or Firm*—Michael N. Meller

[57] ABSTRACT

An optical detection system capable of detecting even small particles or defects on a specimen such as a mask with high sensitivity and being unaffected by diffracted light from the edges of the pattern even when inspecting a thick specimen. The optical detection system includes a light emission means for illuminating a pattern surface on the specimen with light, a first light reception optical system placed on the pattern surface side of the specimen for receiving scattered light emanating from the pattern surface, a second light reception optical system placed on the glass side of the specimen in symmetry with the first light reception optical system relative to the pattern surface for receiving scattered light emanating from the pattern surface through the specimen and a corrective optical element for correcting for differences in the aberration states of the first and second light reception optical systems.

15 Claims, 7 Drawing Sheets

OPTICAL DETECTION SYSTEM FOR DETECTING DEFECTS AND/OR PARTICLES ON A SUBSTRATE

FIELD OF THE INVENTION

The present invention relates to an optical detection system for use in detecting the presence of defects and/or particles on the surface of a transparent or semi-transparent substrate such as a mask in the manufacture of semiconductor devices, liquid crystal display devices, etc.

BACKGROUND OF THE INVENTION

Semiconductor device fabrication includes, for example, a process in which a pattern formed on a mask is transferred to a photosensitive substrate. During this process, if there is any defects and/or particles, e.g. dust, etc., adhering to the surface of the mask on which the pattern is formed, the image of the defects and/or particles will also be transferred to the substrate and cause circuit pattern defects. Therefore, before performing the pattern-transfer exposure, the pattern surface of the mask must be inspected for defects and/or particles, using a defects and/or particles optical detection system.

An example of an optical inspection system for detecting the presence of defects and/or particles on a pattern surface of a mask (reticle) is disclosed in Japanese Laid-Open patent H 5-87549. This optical system has a scanning optical system placed over the pattern side of the mask, and a light reception optical system placed over the same side.

A defect inspecting system using conventional technology is also disclosed in U.S. Pat. No. 4,468,120. This system employs a reception optical system arranged at a position in which diffracted light beams through the mask material will not enter.

The optical detection system of present invention employs a first light reception optical system placed on the pattern surface side of the mask, a second light reception optical system placed on the side of the mask opposite the pattern side and a corrective optical element for correcting differences in aberration states of the first and second optical systems. The light reception optical system of the present invention is arranged at a position at which it can receive both scattered light from defects on the mask and diffracted light from patterns on the mask. An alternative apparatus for detecting defects on a mask using both a reflection detection system and a transmission detection system is taught and described in Applicants corresponding copending U.S. Pat. application Ser. No. 08/636,511, entitled "Apparatus For Detecting Defects on A Mask", the disclosure of which is herein incorporated by reference.

The object of the present invention is to provide an optical detection system that is capable of detecting even small defects and/or particles on the surface of a mask with high sensitivity, unaffected by diffracted light from the edges of the patterns even when inspecting surface patterns on thick masks.

SUMMARY OF THE INVENTION

The optical detection system of the present invention detects defects and/or particles on a specimen having a pattern surface on one side thereof substantially independent of the thickness of the specimen and comprises:

a light emission means for illuminating the pattern surface side of the specimen with light, a first light reception optical system placed on the pattern surface side of the specimen for receiving scattered light emanating from the pattern surface, a second light reception optical system placed on the side of the mask opposite the pattern side and aligned in a position of symmetry with the first light reception optical system relative to the pattern surface for receiving scattered light emanating from the pattern surface which passes through the specimen, and at least one corrective optical element for correcting the differences in the aberration states of the first and second light reception optical systems based on the difference between the amount of scattered light received through the first light reception optical system and the amount of scattered light received through the second light reception optical system.

According to a preferred embodiment of the present invention, a corrective optical element is provided for at least one of the first and second light reception optical systems although a plurality of different corrective optical elements may be used configured to be freely insertable into, and retractable from, the light path, so that the corrective optical elements can be exchanged in response to changes in the index of refraction and thickness of the specimen.

Specifically, the corrective optical element for use in the optical detection system of the present invention may be represented by parallel-plane plates preferably of a thickness that is substantially the optical equivalent or conjugate of the thickness of the specimen, and is placed in either the objective space or image-conjugate space of the first light reception optical system. Alternatively, the corrective optical element may comprise a cylindrical lens placed in the proximity of the pupil of the first or second light reception optical system.

The defects and/or particles detection optical detection system of the present invention includes a first light reception optical system on the pattern side of the specimen under inspection (e.g. a mask) and a second light reception optical system on the reverse (glass) side thereof with each symmetrically positioned with respect to the pattern surface. Therefore, light scattered by the pattern surface is received by the first light reception optical system directly whereas the second light reception optical system receives scattered light through the thickness of the inspection specimen. This causes a difference between the aberration states of the first and second light reception optical systems which could degrade the detection sensitivity of the inspection system by preventing the effect of scattered light from the pattern from being completely eliminated.

The present invention employs a corrective optical element to correct for aberration state differences caused by having the specimen under inspection placed between a first and second light reception optical system on opposite sides of the specimen. Specifically at least one corrective optical element is provided, associated with either the first or the second light reception optical system. The action of the corrective optical element enables the aberration states from the light reception optical system at the pattern side of the inspection specimen and from the light reception optical system at the reverse side of the inspection specimen to be substantially matched. Therefore, for equivalent scattered light emanating from the pattern edge, the light energy of the scattered light received through the pattern-side light reception optical system will be equal to that received through the reverse-side light reception optical system. Thus, when using light reception optical systems having a high numerical aperture even small defects and/or particles can be detected with high sensitivity without being affected by diffracted light from the edges of the pattern. This applies even when inspecting items such as thick masks.

Recently, however, manufacturers have been using thicker masks which reduce the effects of flexure and permit finer patterns to be printed thereon. If the corrective optical system does not exist, the optical paths between the spot on the mask and detectors associated with two light reception optical systems are different because of the thickness of the mask which is significant for a thick mask. Because the effects of aberration variations due to mask thickness are likely to become evident at field stops provided in the light reception optical system on the glass side of the mask, effects of scattered light from the pattern (especially, the edge of the pattern) are eliminated. It is not desirable that aberrations states are different since it is not possible to completely eliminate the effects of scattered light from the pattern (especially, the edge of the pattern) and, therefore, the detection sensitivity of the system is degraded.

BRIEF DESCRIPTION OF THE PREFERRED EMBODIMENTS

Figure 1:
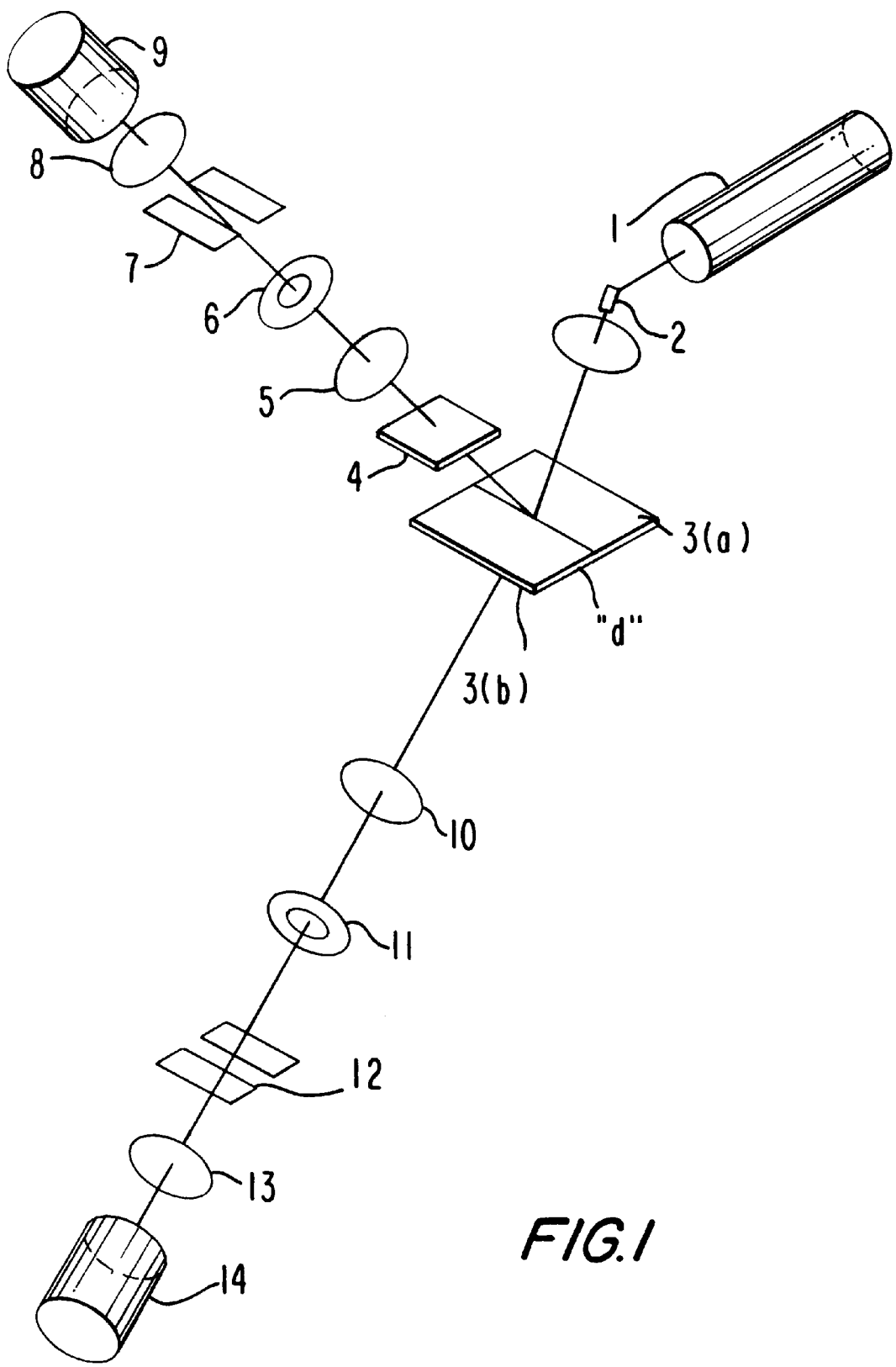
FIG. 1 shows an oblique view of a simplified schematic representation of a configuration of a first embodiment of the defects and/or particles optical detection system of the present invention.

Referring now to the first embodiment of the present invention as illustrated in FIG. 1. Laser light source 1 emits light which passes through scanning optical system 2 to form a scan spot on the pattern surface of the substrate i.e. mask 3 representing the specimen to be inspected for the presence of defects. The substrate has a thickness "d" and the pattern is formed on the upper or top surface (pattern surface side) 3(a) of the mask. The pattern constitutes the pattern surface of the mask. Light scattered from the pattern surface side 3(a) of the specimen 3 is collected through parallel-plane plates 4 and a light reception optical system 5; and is then guided through aperture stop 6, field stop 7, and field lens 8, to the photoelectric surface of a photo-electric conversion device 9. The light reception optical system 5 is an optical system for condensing scattered light and may comprise either an objective lens (refractive optical system) or a condenser lens (reflective optical system). The pattern surface and field stop 7 are conjugates and the aperture stop 6 and the photoelectric surface of photo-electric conversion device 9 are also conjugates. Parallel-plane plates 4 function as the corrective optical element of the optical detection system of the present invention.

Light that is scattered by the pattern surface of mask 3 toward the glass side 3(b) of the mask, i.e. onto the glass side 3(b) opposite to or reverse of the pattern surface side 3(a), must pass through the thickness "d" of the mask 3. This light is then collected by a light reception optical system 10 which is the equivalent of reception optical system 5, whereupon it is then guided through aperture stop 11, field stop 12, field lens 13, and then finally to the photoelectric surface of photo-electric conversion device 14. Here, the pattern surface and field stop 12 are conjugates and aperture stop 11 and the photoelectric surface of photo-electric conversion device 14 are also conjugates. The components used for photo-electric conversion devices 9 and 14 could be, for example, photomultipliers, SPDs (silicon photodiodes), etc. as is well known to those skilled in the art.

In this manner, light reception optical system 5, aperture stop 6, field stop 7, field lens 8, and photo-electric conversion device 9, make up what will hereafter be referred to as the "pattern-side photodetector". Similarly, light reception optical system 10, aperture stop 11, field stop 12, field lens 13, and photo-electric conversion device 14, make up what will hereafter be referred to as the "glass-side photodetector". The pattern-side photodetector and glass-side photodetector are substantially equivalent to one another and should be symmetrically positioned relative to the pattern surface.

Scattered light due to the defects on the mask are generated at different intensities depending on the angle with respect to the mask. Therefore the intensity of scattered light detected by the reception optical system disposed on the pattern side and the intensity of scattered light detected by the reception optical system disposed on the glass surface side are different. However, the intensities of diffracted light on the pattern side and the glass surface side of the mask are approximately equal. For this reason if one compares the output from the reception optical system arranged on the mask side to the output of the reception optical system arranged on the glass surface side the defects on the mask can be observed.

Figure 2A:
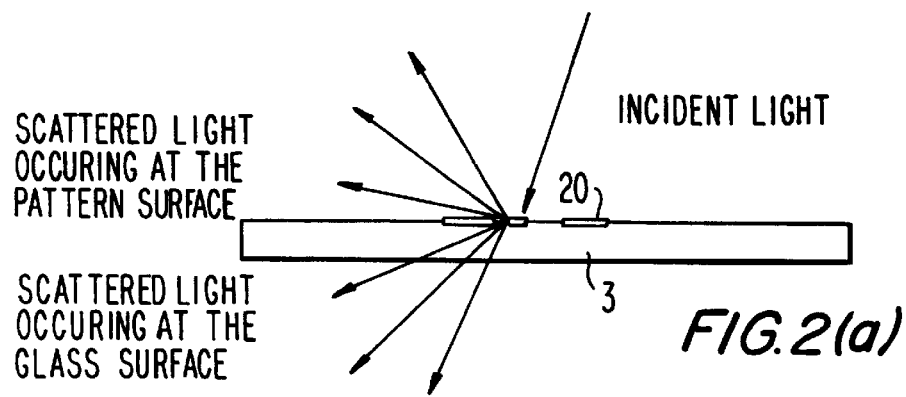
FIGS. 2a, 2b and 2c show states of scattered light occuring at the pattern surface of the specimen under inspection in response to incident light.
Figure 2B:
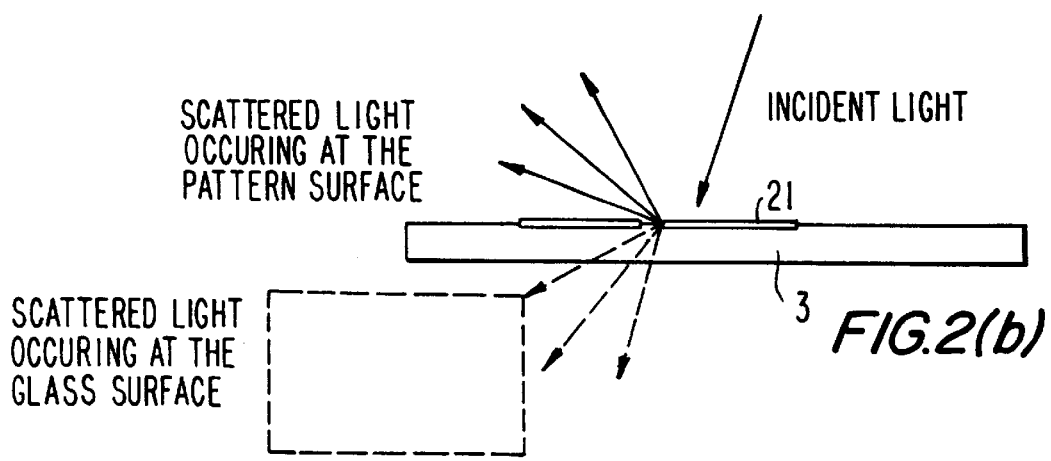
Figure 2C:
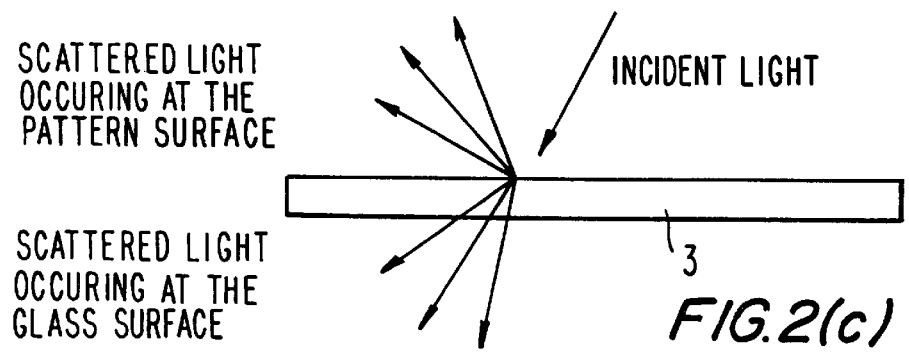

FIGS. 2a, 2b and 2c, shows states of scattered light occurring at the pattern surface in response to incident light and will hereafter be used to explain the principles of detection in accordance with the present invention.

When light is incident upon the pattern surface of mask 3 as shown in FIG. 2(a), the distribution of scattered light from the edge of the pattern 20 (including diffracted light) is substantially symmetrical. Therefore, the intensity of the light passing through aperture stop 6 of the pattern-side photodetector is approximately equal to the intensity of the light passing through aperture stop 11 of the glass-side photodetector. In other words, the difference between the light intensity signal obtained from photo-electric conversion device 9, which has been placed in conjugate, in the pattern-side photodetector, to aperture stop 6, and the light intensity signal obtained from photo-electric conversion device 14, which has been placed in conjugates in the glass-side photodetector, to aperture stop 11, is substantially zero.

FIG. 2(b) shows light striking defects and/or particles on a pattern 21 made of a material that has light-shielding properties, such as chrome. In this case, scattered light from the particle enters the pattern-side photodetector, but does not pass through (as shown by the dotted lines) the glass-side photodetector because it is blocked by the light-shielding pattern. Thus, based on the difference between the light intensity signals obtained from photo-electric conversion device 9 in the pattern-side photodetector, and photo-electric conversion device 14 in the glass-side photodetector, the system can tell whether or not there is foreign matter on the pattern.

FIG. 2 (c) shows light striking a particle and/or defect adhering to a transparent area on the mask 3 where no pattern is formed. In this case, the intensity of scattered light from the particle varies as a function of the scattering angle (the angle between the direction of incidence of the incident light and the direction in which the scattered light proceeds).

Figure 3:
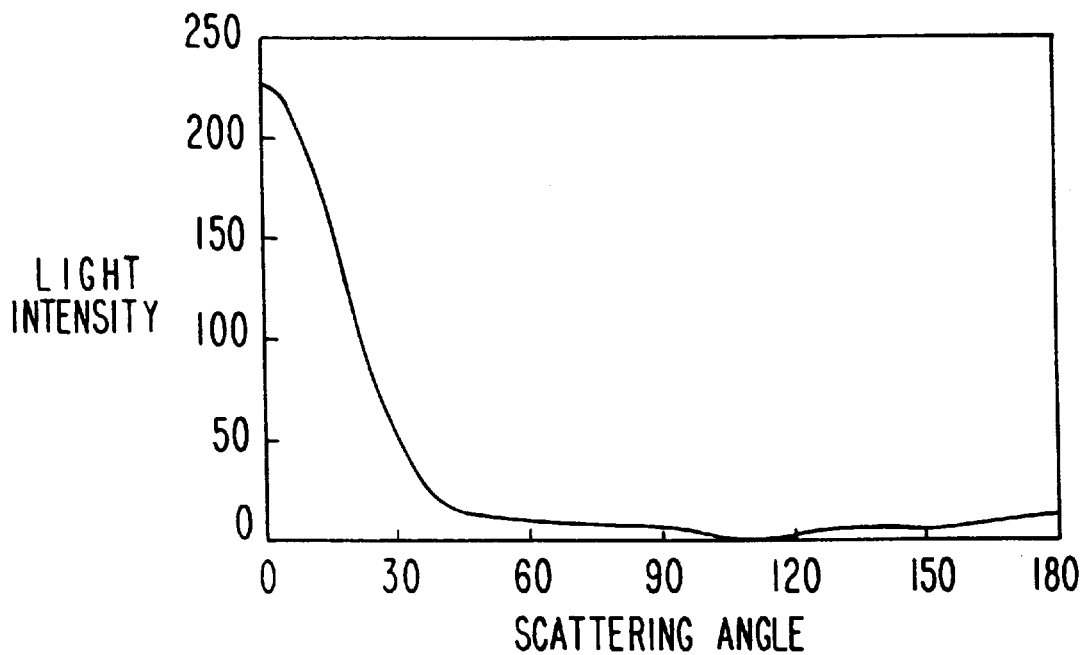
FIG. 3 shows the scattering angle characteristic for scattered light from a minute particle, i.e. the relationship of the scattering angle to the light intensity of the scattered light from the particles and/or defects.

FIG. 3 shows the scattering angle characteristic for scattered light from a minute particle (i.e., the relationship of the scattering angle to the light intensity of the scattered light from the particle).

As can be seen from FIG. 3, for a foreign particle of a size detectable by the present invention (e.g., a particle with a diameter on the order of 0.3 μm), the smaller the scattering angles the greater the light intensity. As shown in FIG. 1, there is a large difference between the scattering angle of scattered light entering from the pattern-side photodetector and the scattering angle of scattered light entering from the glass-side photodetector. Thus, based on the difference between the light intensity signals obtained from photo-electric conversion device 9 in the pattern-side photodetector, and photo-electric conversion device 14 in the glass-side photodetector, the system can tell whether or not there is defects and/or particles on the transparent area.

In general, because scattered light from defects and/or particles is of extremely low intensity, if random light, etc., gets mixed in with the scattered light in the photodetectors and manages to get as far as the photo-electric conversion devices, it can become impossible to accurately detect scattered light from defects and/or particles. Because of this, a field stop 7 and 12 is placed in both photodetectors of the defects and/or particles inspection system of FIG. 1, which are then positioned conjugate to the pattern surface. It is the action of these field stops 7 and 12, that keep random light from reaching the photo-electric conversion devices. Also, in order to prevent the system from being affected by diffracted light from the edges of the pattern, aperture stop 6, in the pattern-side photodetector, and aperture stop 11, in the glass-side photodetector, must be positioned in precise symmetry with each other, relative to the pattern surface. Once this is done the angles of incidence of the diffracted light into the two aperture stops will be equal, and will therefore not produce a false difference signal.

As discussed earlier, however whereas the photodetectors on the pattern side of the mask receive the scattered light with no intervening mask 3, the photodetectors on the glass side receive scattered light through an intervening mask 3. Therefore, in spite of the fact that the positioning of the pattern-side photodetector and the glass-side photodetector are precisely symmetrical with respect to the pattern surface, and that the field stop in each of the photodetectors is positioned in a precisely conjugate relationship to the pattern surface, the effects of aberration such as astigmatism and coma rising through the mask 3 can cause a difference between the light energy of the diffraction light from the pattern edges that passes through pattern-side field stop 7, and the light energy of the diffraction light from the pattern edges that passes through glass-side field stop 12. Moreover, the thicker the mask 3 is, the more pronounced this trend becomes. Therefore, in order to make the light energy passing through field stop 7 the same as that passing through field stop 12 (for equivalent scattered light emitted from the pattern edge), a corrective optical element is introduced into at least one of the light paths which will make the aberration states of the pattern side photodetector and glass side photodetector the same.

In this embodiment, the aberration states of the pattern-side and glass-side photodetectors are substantially matched by inserting, as a corrective optical element, a parallel-plane plate 4, preferably having the same thickness and index of refraction as mask 3, into the objective space of the pattern-side light reception optical system 5 and in a position parallel to mask 3. When this is done, this corrective optical element makes the amount of light that passes through pattern-side photodetector field stop 7 equal to that which passes through glass-side photodetector field stop 12, resulting in equivalent amounts of scattered light emanating from the pattern edge. As a result, the system is able to effect positive detection of scattered light from defects and/or particles based on the difference between the light intensity signals obtained by pattern-side photo-electric converter 9 and glass-side photo-electric converter 14, unhampered by the effects of diffracted light from the pattern edge.

The system can also be used to inspect items of different thicknesses. All that is required, for example, to alternate between inspection of a 0.09-inch-thick mask and 0.25-inch-thick mask, is to remove the currently-installed parallel-plane plate 4 and replace it with one of a thickness corresponding to that of the mask to be inspected. Once this has been done, the system will be able to positively detect scattered light from defects and/or particles on masks of different thicknesses, unhampered by the effects of diffracted light from the pattern edge. Moreover, because parallel-plane plate 4 is placed just ahead of light reception optical system 5, the light beam is fairly diffused after it passes through parallel-plane plates 4. Therefore, even if the surface precision of parallel-plane plates 4 are not very high in comparison to that of mask 3, and even if they have defects and/or particles or scratches on them, the effects of these imperfections will be removed by the action of field stop 7 and aperture stop 6. In this manner, then, in this first working example, if the system uses a light reception optical system having a large numerical aperture, it is possible to detect small particles and/or defects, unhampered by the effects of diffracted light from the pattern edge, even on an inspection specimen such as a thick mask.

Figure 4:
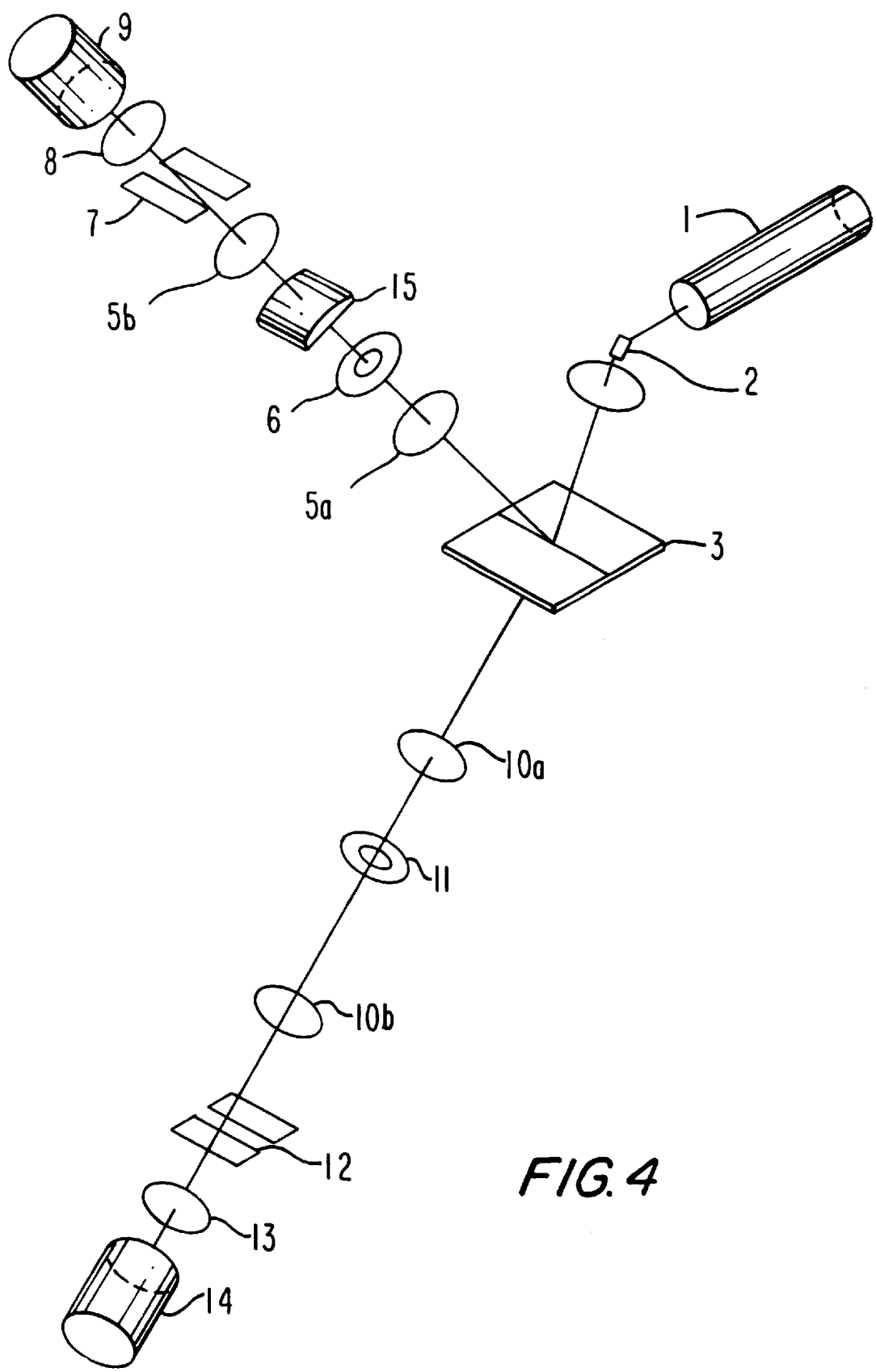
FIG. 4 shows an oblique view of a simplified schematic representation of a second embodiment of the defects and/or particles optical detection system of the present invention.

FIG. 4 is an oblique view showing a simplified schematic representation of the configuration of the second embodiment of the present invention. The second embodiment is described below with the explanation focusing mainly on how this embodiment differs from the first one.

The configuration of the second embodiment is nearly the same as that of the first embodiment. The only significant difference between the two systems is that in the second embodiment, parallel-plane plate 4, which was used as the corrective optical element in the first embodiment, is replaced by a cylindrical lens (15), placed near the pupil of the light reception optical system (5a and b). Accordingly, elements of FIG. 4 that have the same functions as elements of FIG. 1 have the same reference numbers as in FIG. 1. The aperature stops 6 and 11 are placed in the field space of the light reception optical system 5a and 5b and is parallel to the image of the mask 3.

Figure 6:
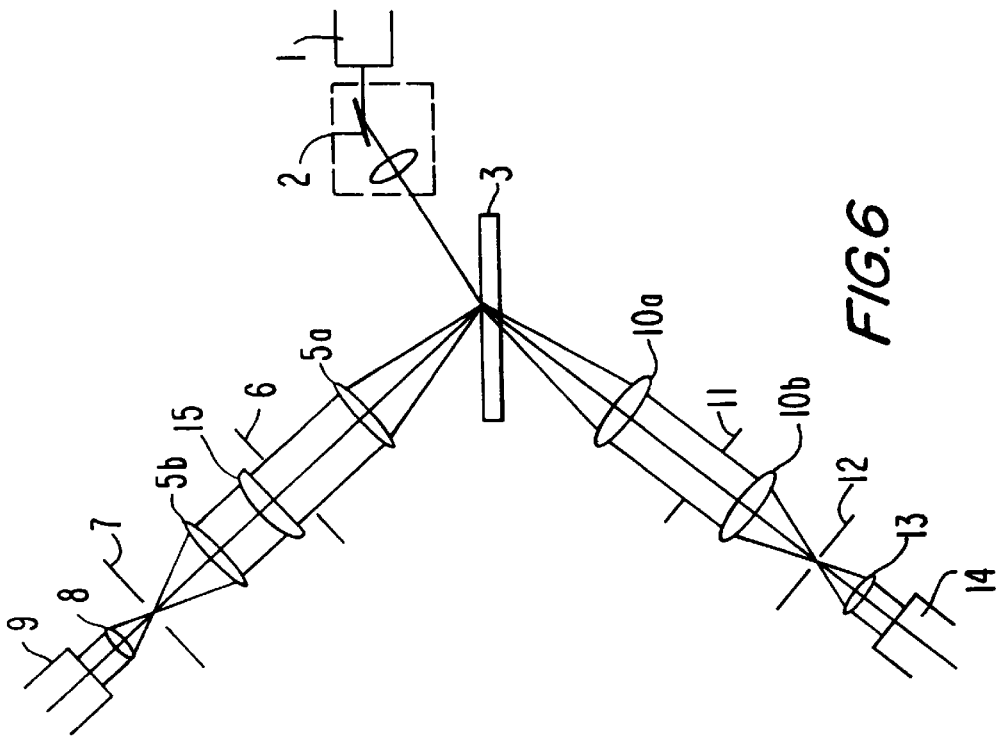
FIG. 6 is a variation of the arrangement of FIG. 5 corrresponding to the second embodiment shown in FIG. 4.
Figure 5:
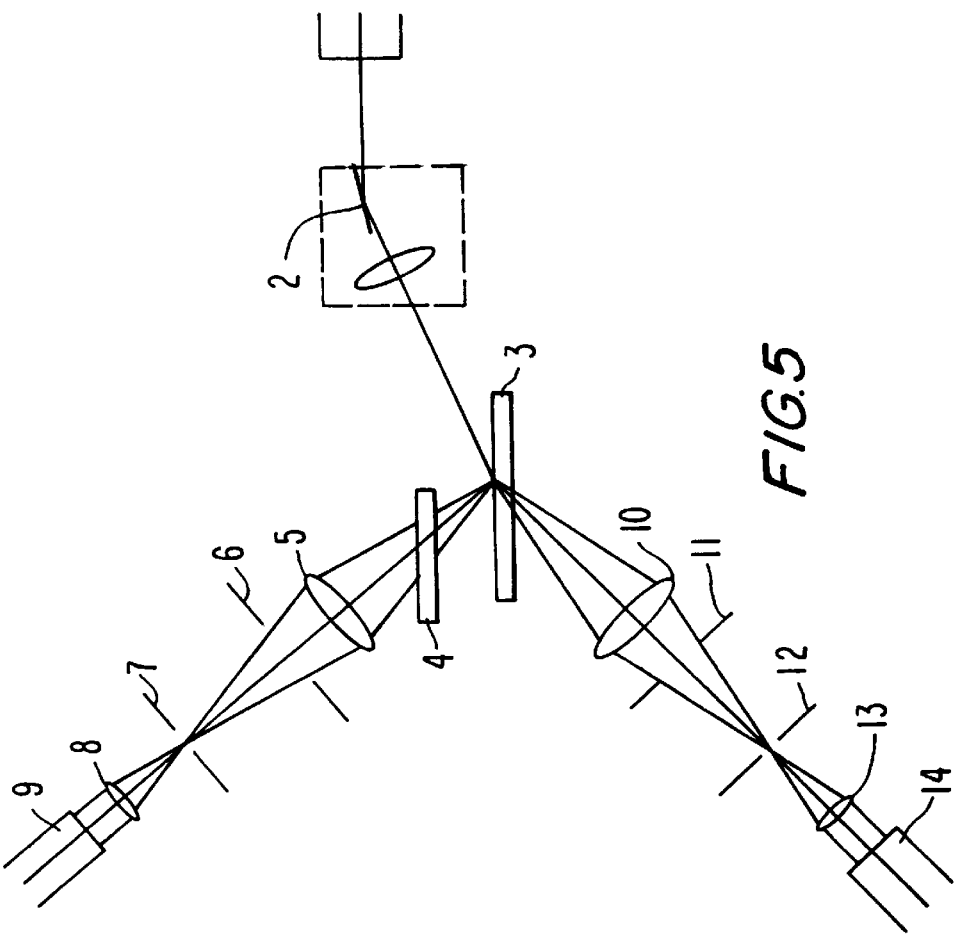
FIG. 5 is a conceptual diagram showing the optical path for the embodiment of FIG. 1 and illustrates the utmost circumference of the light beam only.

Functions of the aperture stops 6 and 11 are described with reference to FIGS. 5 and 6 in which FIG. 5 is a conceptual diagram showing the optical path for the embodiment of FIG. 1 and FIG. 6 being a conceptual diagram showing the optical path for the embodiment of FIG. 4.

Aperature stops 6 and 11 are arranged to form cubic angles (equivalent to the numeral aperatures of the reception optical system 5 and 10) for capturing scattered light throughout the scanning region on the mask 3. With this configuration, the uniformity of detection sensitivies of the system can be obtained. The aperature stops 6 and 11 define the entrance pupil of the reception optical system 5 and 10. In the system of FIGS. 1 and 5 the reception optical system 5 and 10 images the image of the mask 3 onto slit 7 with the scattered light from mask 3. In the arrangement of FIGS. 4 and 6, the reception optical system is constructed with lens 5a and 5b which image the image of the mask 3 onto slit 7 using the scattered light from mask 3. In this system light from mask 3 is converted into parallel beams by lens 5a. These parallel beams are condensed by lens 5b over slit 7. The image in the scanning region, which is part of the mask 3, is formed on the slit 7. Cylindrical lens 15, as the corrective optical element, is disposed between lens 5a and 5b, and is located inside the receiving optical system.

In FIG. 5, when there is no limitation in the size of the system etc., it is preferable that the stop 6 be located at the back focal plane of the reception optical system 5 and that stop 11 be located at the back focal plane of reception optical system 10. In this way reception optical systems 5 and 10 can be an objective telecentric optical system. In the arrangement of FIG. 6 when there is no limitation in the size of the system etc., it is preferable that the stop 6 be located at the back focal plane of 5a of the reception optical system and that stop 11 be located at the back focal plane of reception optical system 10. When the reception optical system is an object side telecentric optical system, it is preferable that the scanning optical system is also a telecentric optical system.

Figure 8:
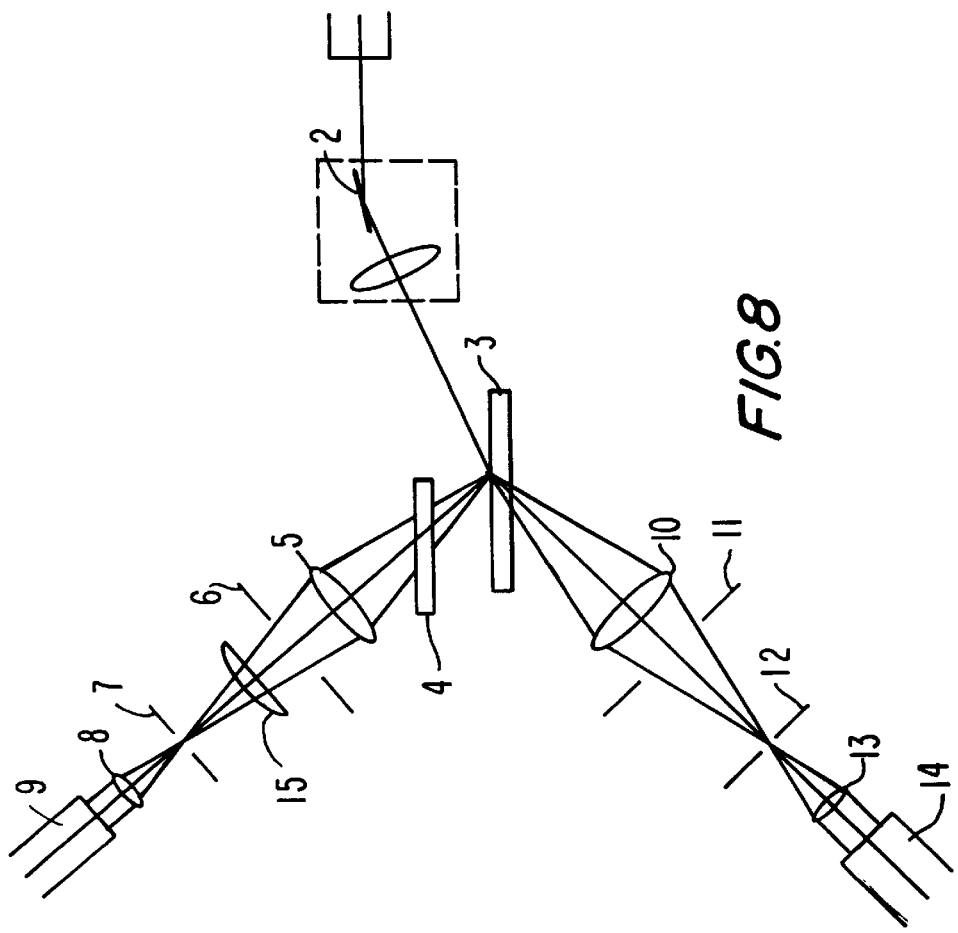
FIG. 8 is a modification of the arrangement of FIG. 5.
Figure 7:
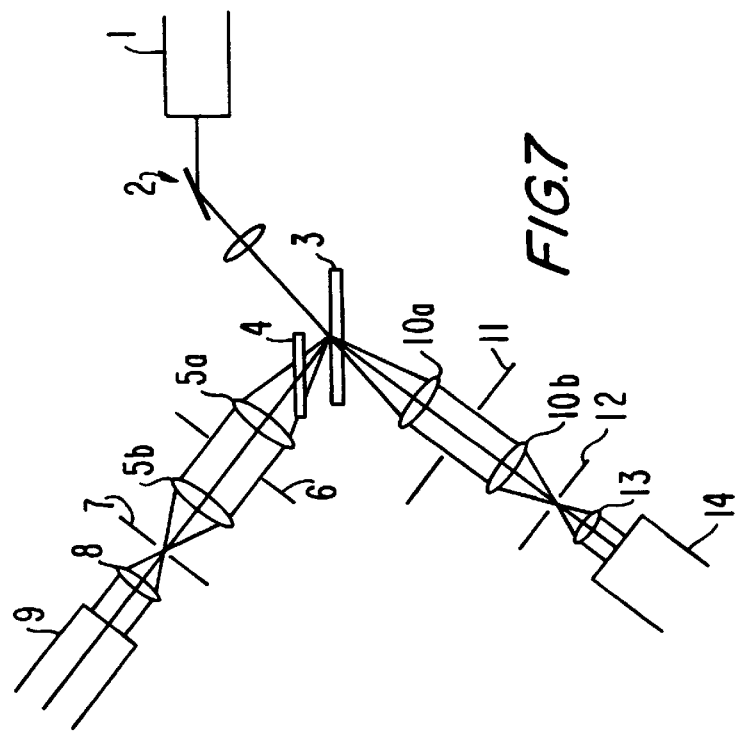
FIG. 7 is a modification of the arrangement of FIG. 6.

The receiving optical systems 5a and 5b may be combined with the corrective element 4 as shown in FIG. 7 so that the receiving optical systems will convert light from a point on mask into parallel beams. This arrangement may be further modified by combining receiving optical system 5 and corrective element 15 as shown in FIG. 8 such that the receiving optical system does not convert light from a point on mask 3 into parallel beams.

For both embodiments 1 and 2 aberrations which are induced by light and which go through mask 3 include astigmatism, coma, and spherical aberrations. When comparing two sets of outputs from detectors 9, 14, imaging conditions must be the same for both sets. (Aberration must be corrected in the same manner.) However, detector 14 receives light affected by the above aberrations through mask 3. Therefore, the present invention stores the element (corrective elements 4, 15) which generates the above aberration in the other set, thus making the resulting imaging conditions the same for both detectors 9, 14.

In the second embodiment, the aberration state of the pattern-side photodetector is approximately matched to that of the glass-side photodetector through the action of cylindrical lens 15, which, as shown in FIG. 4, is placed near the pupil of light reception optical system 5a, 5b. The curvature and index of refraction of cylindrical lens 15 in this configuration is a function of the thickness and index of refraction of the inspection specimen, i.e., the mask 3.

Figure 9:
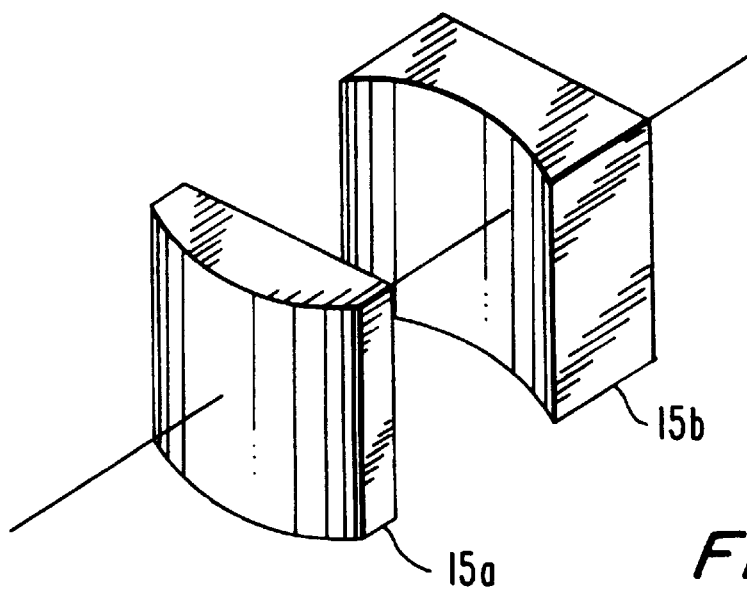
FIG. 9 shows a simplified diagram of a modified version of the corrective optical member used in the second embodiment as shown in FIG. 4.

In this second embodiment, a mask 3 of a different thickness can be inspected by replacing the cylindrical lens 15 with one having a curvature corresponding to the thickness of the new mask 3 to be inspected. As an alternatives as shown in FIG. 9, a pair of cylindrical lenses comprising, for examples a cylindrical lens 15a having positive refractive power and cylindrical lens 15b having negative refractive power, may be used. When this configuration is used, the space between the two lenses of the cylindrical lens pair can be adjusted, as appropriate for the thickness of the mask 3 currently being inspected, in order to match the aberration state of the pattern-side photodetector to that of the glass-side photodetector.

Figure 10:
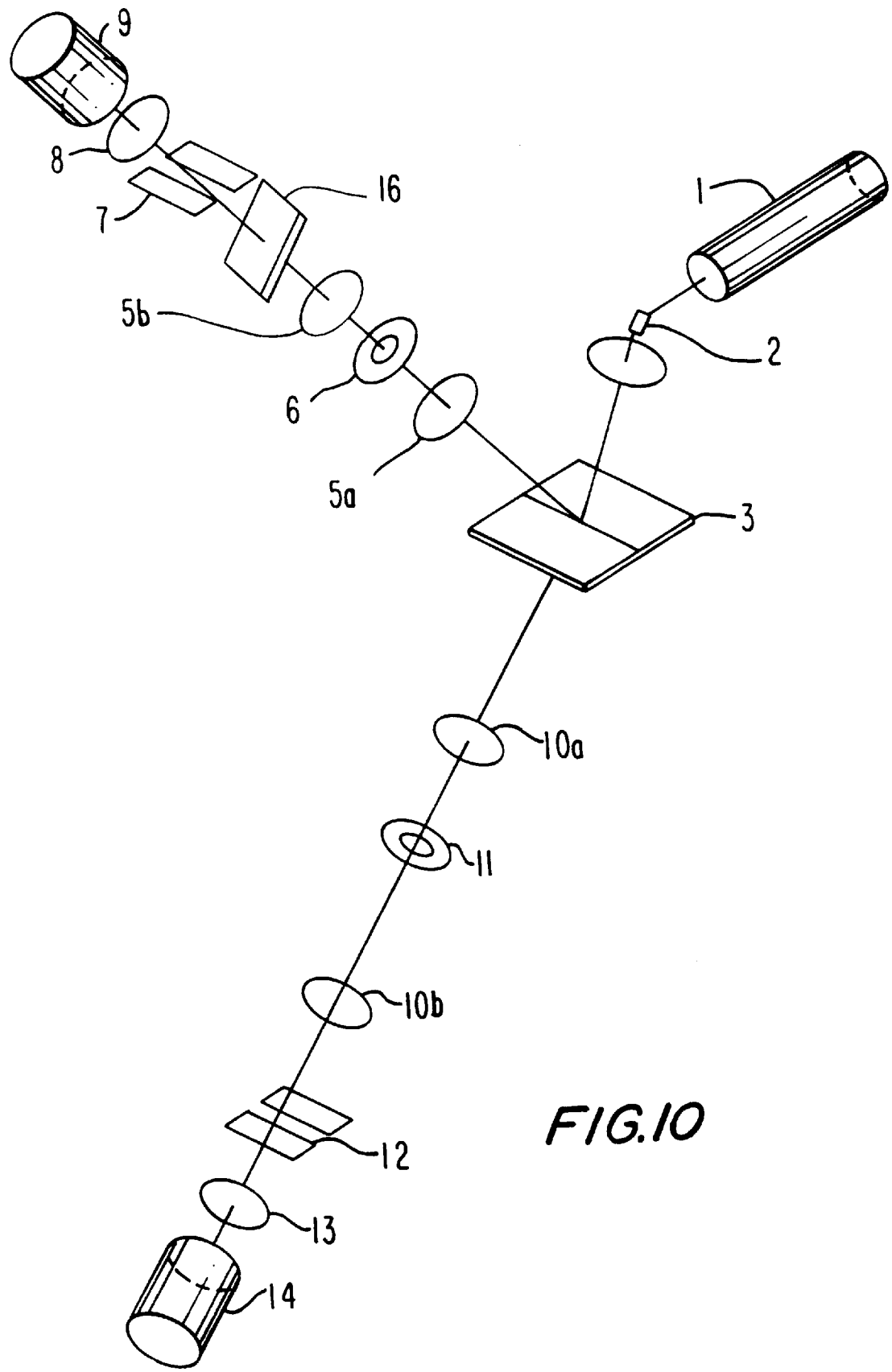
FIG. 10 shows an oblique view of a simplified schematic representation of a third embodiment of the defects and/or particles optical detection system of the present invention.

FIG. 10 is an oblique view showing a simplified schematic representation of a third embodiment of the present invention.

The configuration of the third embodiment is also nearly the same as that of the first embodiment. The significant difference between this system and the first embodiment is that in this third embodiment, parallel-plane plates 4, which were used as the corrective optical element in the first embodiment, are replaced by parallel plane plates 16, which are placed in the field space of light reception optical system (5a and 5b). Accordingly, elements of FIG. 10 that have the same functions as elements of FIG. 1, have the same reference numbers as in FIG. 1. The third embodiment is described below, focusing primarily on how it differs from the first embodiment.

In the third embodiment as shown in FIG. 10, the aberration state of the pattern-side photodetector is approximately matched to that of the glass-side photodetector through the action of parallel-plane plates 16, which have the same index of refraction as mask 3, aperature stop 6 is placed in the field space of light reception optical system (5a and 5b) which are positioned parallel to the image of mask 3. In this configuration, the thickness of parallel-plane plates 16 is a function of the magnification ratio of light reception optical system (5a and 5b), and the thickness of the inspection specimen, mask 3.

It goes without saying, of course, that in this third embodiment, a mask 3 of a different thickness can be inspected by replacing the parallel-plane plate with one that is appropriate for the thickness of the new mask 3 to be inspected. In general, light reception optical systems with a high numerical aperture tend to have a small objective space. In this situation, in a configuration such as that of the third embodiment, it is best to place the corrective optical element in the field space or image-conjugate space of the light reception optical system.

Shown in the above first and third embodiments, were situations in which parallel-plane plates having the same index of refraction as mask 3 were used as corrective optical elements. Parallel-plane plates having a different index of refraction from that of the mask could, however, also be used. To do this, the parallel-plane plates must be tilted at a prescribed angle with respect to the mask or its image, and must be of a thickness that is optically equivalent to or a conjugate to the thickness of the mask.

Also, in the second embodiment, the cylindrical lens 15, which was used as a corrective optical element, was provided in the pattern-side light reception optical system. The cylindrical lens 15 could, however, have been provided in the glass-side light reception optical system, or even in both the pattern-side and glass-side light reception optical systems.

In addition, although the above embodiments were described for the case in which the inspection specimen was a mask, the present invention may also be used for inspections of other transparent inspection specimens with a pattern formed on one side.

As described above, in the present invention, the aberration state of a pattern-side light reception optical system is approximately matched to that of a glass-side light reception optical system through the action of a corrective optical element. Because of this, even when light reception optical systems with a high numerical aperture are used, even small particles and/or defects can also be detected with high sensitivity, without being affected by diffracted light from the edges of the pattern, even when inspecting items such as thick masks.

In embodiment 1 lens or mirrors (reflection systems) of the same design can be used for reception optical systems 5 and 10. In the same manner, in embodiments 2 and 3, lenses and mirrors (reflection systems) of the same design can be used for lens 5*a* and lens 10*a,* and lens 5*b* and lens 10*b*. Now, if one changes the design of a set of system 10 (10*a,* 10*b*) on the transmittive side of the mask 3 from the other set of reception optical system 5 (5*a,* 5*b*), it will be difficult to create the same level of aberration correction on the detector side due to the stringent aberration specification which must be met.

We claim:

1. An optical detection system for detecting defects and particles on a pattern surface of an inspected specimen with a pattern formed thereon, comprising:
    a light emission means for illuminating said pattern surface with light;
    a first light reception optical system placed on the pattern surface side of said specimen for receiving scattered light emanating from said pattern surface;
    a second light reception optical system, placed on the side opposite said pattern side of said specimen and aligned in a position of symmetry with said first light reception optical system relative to said pattern surface for receiving scattered light emanating from said pattern surface which passes through said specimen; and
    at least one corrective optical element for correcting for differences in the aberration states of said first and second light reception optical systems based on a difference between the amount of scattered light received through said first light reception optical system and the amount of scattered light received through said second light reception optical system.

2. The optical detection system of claim 1, wherein said corrective optical element is present in at least one of said first and second light reception optical systems.

3. The optical detection system of claim 2, which comprises a plurality of different corrective optical elements.

4. The optical detection system of claim 2, wherein said corrective optical element is defined by parallel-plane plates having thicknesses which substantially correspond to the optical equivalent or conjugate of the thickness of said specimen.

5. The optical detection system of claim 4, wherein said parallel-plane plates are placed in either an objective space or the image-conjugate space of said first light reception optical element.

6. The optical detection system of claim 5, wherein said parallel plane plates have substantially the same index of refraction as said specimen.

7. The optical detection system of claim 6, wherein said parallel plane plates are substantially equivalent and are placed substantially parallel to said specimen or an image thereof.

8. The optical detection system of claim 2, wherein said corrective optical element comprises a cylindrical lens placed in proximity of the pupil of said first or second light reception optical system.

9. The optical detection system of claim 8, wherein each corrective optical element is selected with an index of refraction and thickness corresponding to said specimen.

10. The optical detection system of claim 2, wherein said corrective optical element comprises a cylindrical lens placed in a proximity of a pupil of said first or second light reception optical system.

11. An optical detection system for detecting defects and particles on a pattern surface of an inspected specimen with a pattern formed thereon, comprising:
    a radiation source;
    a scanning optical system, said pattern surface is illuminated by radiation from said radiation source via said scanning optical system;
    a first radiation reception optical system placed on the pattern surface side of said specimen;
    a second radiation reception optical system placed on the side opposite said pattern side of the specimen;
    a first detector connected to said first radiation reception optical system;
    a second detector connected to said second radiation reception optical system; and
    at least one corrective optical member placed between the specimen and the second detector;
    wherein when the radiation passes through said corrective optical member, said corrective optical member provides aberration substantially the same as aberration from said specimen.

12. The optical detection system of claim 11, wherein said aberration is selected from the group consisting of astigmatism, coma and spherical.

13. The optical detection system of claim 11, wherein elements of said first radiation reception optical system and elements of said second radiation reception optical system are the same.

14. The optical detection system of claim 11, wherein optical axes of said first and second radiation reception optical systems are inclined against said specimen surface.

15. The optical detection system of claim 11, wherein said first and second radiation reception optical systems are placed where said first and second radiation reception optical systems can receive both scattered radiation from said defects and/or particles on the specimen and detracted radiation from said pattern.

* * * * *